US012741947B2

(12) United States Patent
Park et al.

(10) Patent No.: US 12,741,947 B2

(45) Date of Patent: Sep. 22, 2026

(54) COMPOUND, METHOD FOR PREPARING SAME, AND SINGLE MOLECULE AND OLIGOMER DERIVED FROM SAME

(71) Applicant: LG CHEM, LTD., Seoul (KR)

(72) Inventors: Beomsu Park, Daejeon (KR); Jihye Jung, Daejeon (KR); Hyun Cheol Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 311 days.

(21) Appl. No.: 18/706,713

(22) PCT Filed: Jan. 17, 2023

(86) PCT No.: PCT/KR2023/000790

§ 371 (c)(1),
(2) Date: May 1, 2024

(87) PCT Pub. No.: WO2023/136701

PCT Pub. Date: Jul. 20, 2023

(65) Prior Publication Data

US 2024/0409520 A1 Dec. 12, 2024

(30) Foreign Application Priority Data

Jan. 17, 2022 (KR) ........................ 10-2022-0006316

(51) Int. Cl.
*C07D 253/02* (2006.01)

(52) U.S. Cl.
CPC .................................. *C07D 253/02* (2013.01)

(58) Field of Classification Search
CPC .................................................... C07D 253/02
See application file for complete search history.

(56) References Cited

U.S. PATENT DOCUMENTS

| | | | |
|---|---|---|---|
| 3,629,255 | A | 12/1971 | Beyleveld et al. |
| 2002/0065372 | A1 | 5/2002 | Wlassics et al. |
| 2020/0157376 | A1 | 5/2020 | Hoshino et al. |
| 2020/0165277 | A1 | 5/2020 | Kubodera et al. |
| 2020/0291147 | A1 | 9/2020 | Bossolo et al. |
| 2021/0206690 | A1 | 7/2021 | Nose |
| 2022/0204690 | A1 | 6/2022 | Nose |

FOREIGN PATENT DOCUMENTS

| | | | |
|---|---|---|---|
| CN | 107739346 | B | 9/2020 |
| EP | 3498756 | A1 | 6/2019 |
| JP | S63-162679 | A | 7/1988 |
| JP | H02-129257 | A | 5/1990 |
| JP | 2005-047880 | A | 2/2005 |
| JP | 2006-036973 | A | 2/2006 |
| JP | 4321922 | B2 | 8/2009 |
| JP | 2012-111856 | A | 6/2012 |
| JP | 6756990 | B2 | 9/2020 |
| KR | 2018-0125155 | A | 11/2018 |
| KR | 2019-0042921 | A | 4/2019 |
| KR | 2019-0134328 | A | 12/2019 |
| KR | 2020-0020682 | A | 2/2020 |
| KR | 2021-0022091 | A | 3/2021 |
| WO | 2019-039186 | A1 | 2/2019 |
| WO | 2021-024964 | A1 | 2/2021 |

OTHER PUBLICATIONS

CAS Registry No. 237081-09-3 (which entered STN Sep. 3, 1999) (Year: 1999).*
International Search Report issued for International Application No. PCT/KR2023/000790 on May 10, 2023, 4 pages.

* cited by examiner

*Primary Examiner* — Kamal A Saeed
*Assistant Examiner* — Quincy McKoy
(74) *Attorney, Agent, or Firm* — ROTHWELL, FIGG, ERNST & MANBECK, P.C.

(57) ABSTRACT

The present specification relates to a compound of Chemical Formula 1, a method for preparing the same, and a single molecule and an oligomer derived from the compound.

5 Claims, 1 Drawing Sheet

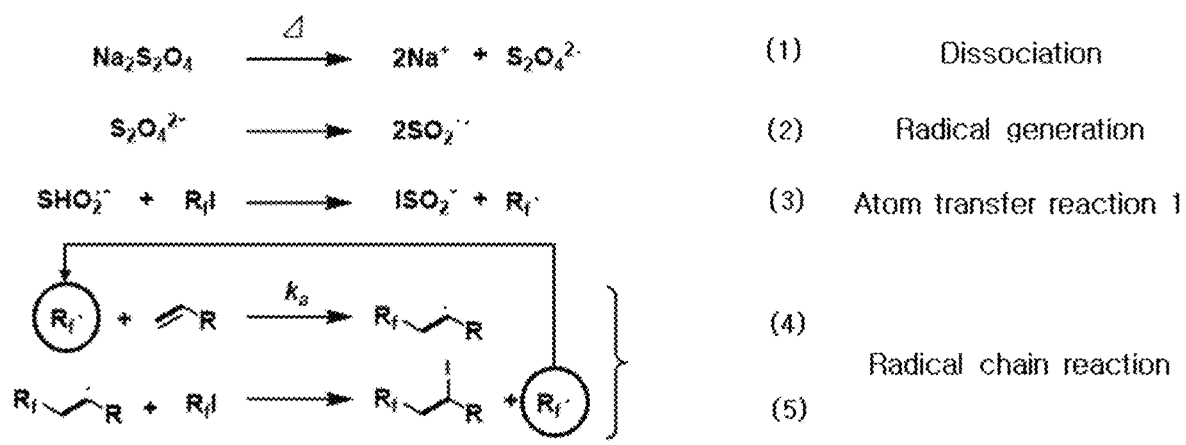
(1) Dissociation
(2) Radical generation
(3) Atom transfer reaction 1
(4)
(5)
Radical chain reaction

COMPOUND, METHOD FOR PREPARING SAME, AND SINGLE MOLECULE AND OLIGOMER DERIVED FROM SAME

This application is a 35 U.S.C. § 371 National Phase Entry Application from PCT/KR2023/000790, filed on Jan. 17, 2023, which claims priority to and the benefit of Korean Patent Application No. 10-2022-0006316 filed in the Korean Intellectual Property Office on Jan. 17, 2022, the entire contents of which are incorporated herein by reference.

TECHNICAL FIELD

The present specification relates to a compound, a method for preparing the same, and a single molecule and an oligomer derived from the compound.

BACKGROUND

Triallyl isocyanurate is useful as a cross-linking agent having excellent heat resistance and chemical resistance, and is expected to be used in a wide range of fields such as electronic materials, liquid crystals, semiconductors, and solar cells. For example, in printed circuit boards, that is, plate-like or film-like parts that constitute electronic circuits by fixing a large number of electronic parts such as integrated circuits, resistors, and condensers to a surface thereof and connecting the parts through wiring, triallyl isocyanurate is used as a sealing material for preventing penetration of materials such as liquids or gases into the parts.

However, triallyl isocyanurate has high relative permittivity and high dissipation factor, so that research has been continuously conducted to reduce them.

SUMMARY

Technical Problem

The present specification provides a compound, a method for preparing the same, and a single molecule and an oligomer derived from the compound.

Technical Solution

An exemplary embodiment of the present specification provides a compound of the following Chemical Formula 1.

[Chemical Formula 1]

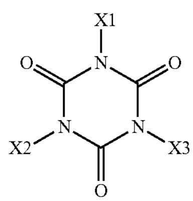

In Chemical Formula 1, at least one of X1 to X3 is

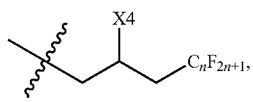

and the others are an allyl group, n is an integer from 1 to 20,

is a moiety bonded to Chemical Formula 1, and

X4 is a halogen group.

An exemplary embodiment of the present specification provides a method for preparing a compound of the following Chemical Formula 1, the method including: (s1) putting triallyl isocyanurate, $C_nF_{2n+1}X4$, a base, and a solvent into a container and stirring the resulting mixture under nitrogen gas; and (s2) adding a radical initiator thereto and stirring the resulting mixture.

[Chemical Formula 1]

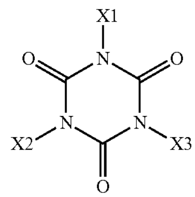

In Step (s1) and Chemical Formula 1, at least one of X1 to X3 is

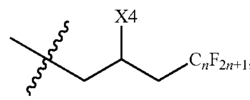

and the others are an allyl group, n is an integer from 1 to 20,

is a moiety bonded to Chemical Formula 1, and

X4 is a halogen group.

Another exemplary embodiment of the present specification provides a single molecule derived from the compound.

Further, still another exemplary embodiment of the present specification provides an oligomer including a monomer derived from the compound.

Advantageous Effects

The compound according to an exemplary embodiment of the present specification, and a single molecule and an oligomer derived therefrom include a good release group and a structure capable of being cross-linked, so that various derivatives can be prepared.

The compound according to an exemplary embodiment of the present specification can be used as a polyfunctional monomer to exhibit the effects of achieving low refractive index, low relative permittivity, low surface energy and low dissipation factor.

In the method for preparing a compound according to an exemplary embodiment of the present specification, the reaction is performed under mild conditions with minimal side reactions, so that the yield of the compound of Chemical Formula 1, which is a target compound, is increased.

BRIEF DESCRIPTION OF DRAWINGS

FIG. 1 is a view describing the mechanism of the method for preparing the compound of Chemical Formula 1.

DETAILED DESCRIPTION

Hereinafter, the present specification will be described in more detail.

An exemplary embodiment of the present specification provides a compound of the following Chemical Formula 1.

[Chemical Formula 1]

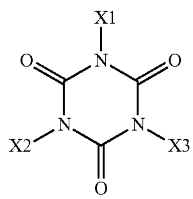

In Chemical Formula 1, at least one of X1 to X3 is

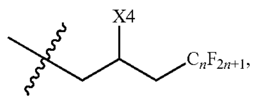

and the others are an allyl group, n is an integer from 1 to 20,

is a moiety bonded to Chemical Formula 1, and

X4 is a halogen group.

The compound of Chemical Formula 1 according to an exemplary embodiment of the present specification includes a perfluoroalkyl group including fluorine having the effects of achieving low relative permittivity and low dissipation factor, and is used as a polyfunctional monomer as a triallyl isocyanurate derivative that serves as a cross-linking agent, so that it is possible to exhibit the effects of achieving low relative permittivity, low surface energy and low dissipation factor.

According to an exemplary embodiment of the present specification, any one of X1 to X3 is

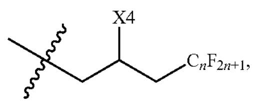

and the others are an allyl group.

According to an exemplary embodiment of the present specification, any two of X1 to X3 are

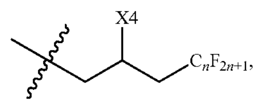

and the other is an allyl group.

According to an exemplary embodiment of the present specification, X1 to X3 are each

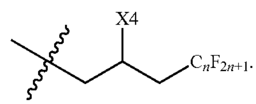

According to an exemplary embodiment of the present specification, n is an integer from 4 to 12.

According to an exemplary embodiment of the present specification, n is 4, 6 or 8.

According to an exemplary embodiment of the present specification, X4 is an iodine group (—I).

According to an exemplary embodiment of the present specification, the

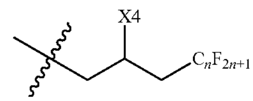

is any one of the following structures.

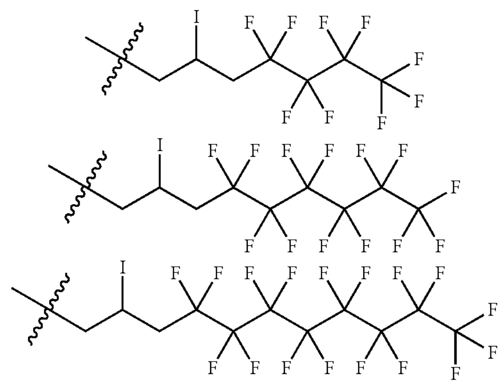

According to an exemplary embodiment of the present specification, when n of the

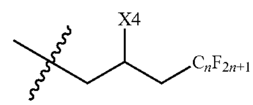

is within the above range, compounds with various molecular weights may be prepared because the chain length of a perfluoroalkyl group is easily adjusted. In addition, when a perfluoroalkyl group is included, it is possible to exhibit effects of achieving low refractive index, low relative permittivity, low surface energy and low dissipation factor.
According to an exemplary embodiment of the present specification, Chemical Formula 1 is any one selected from the following compounds.
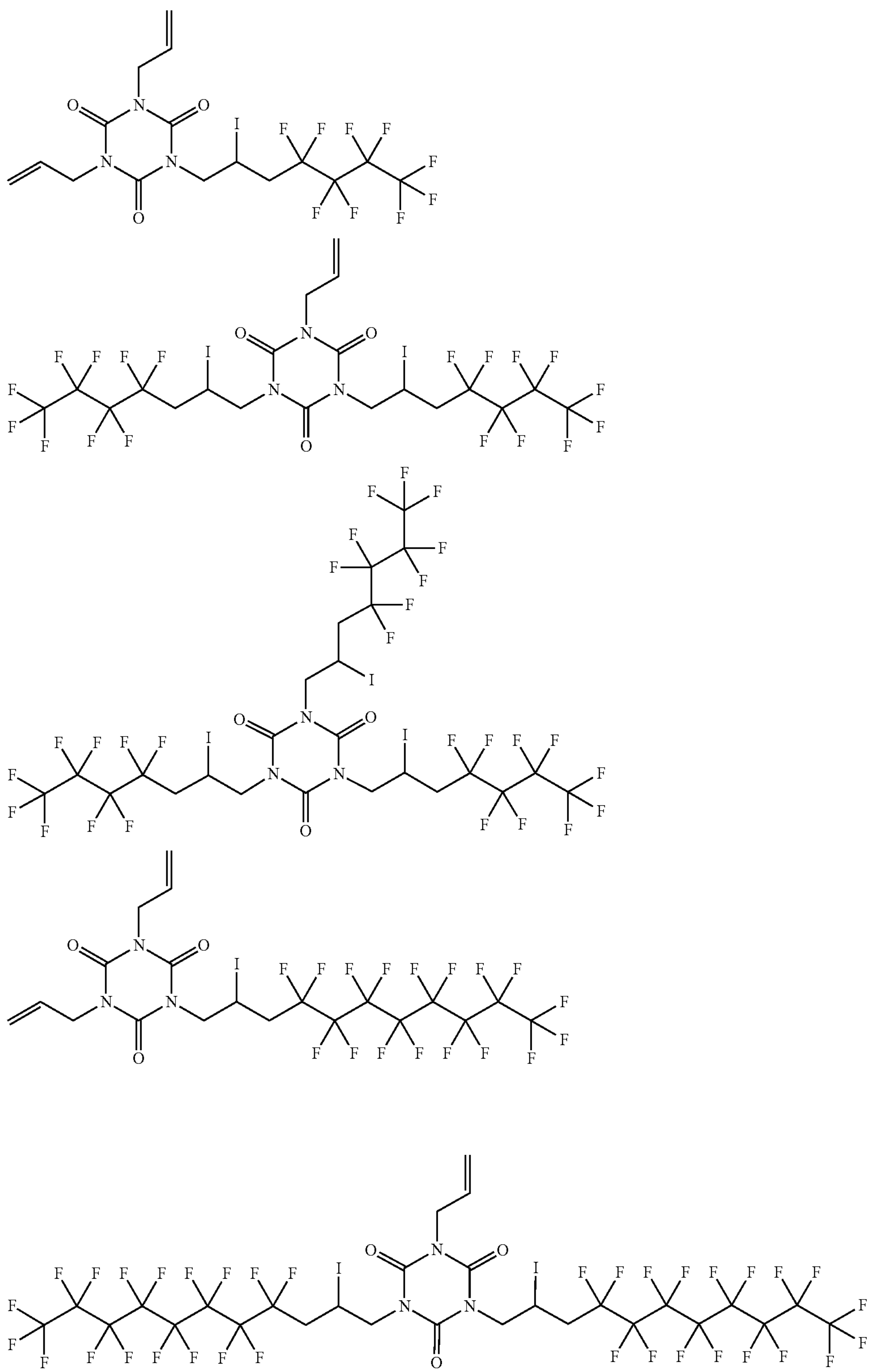

-continued
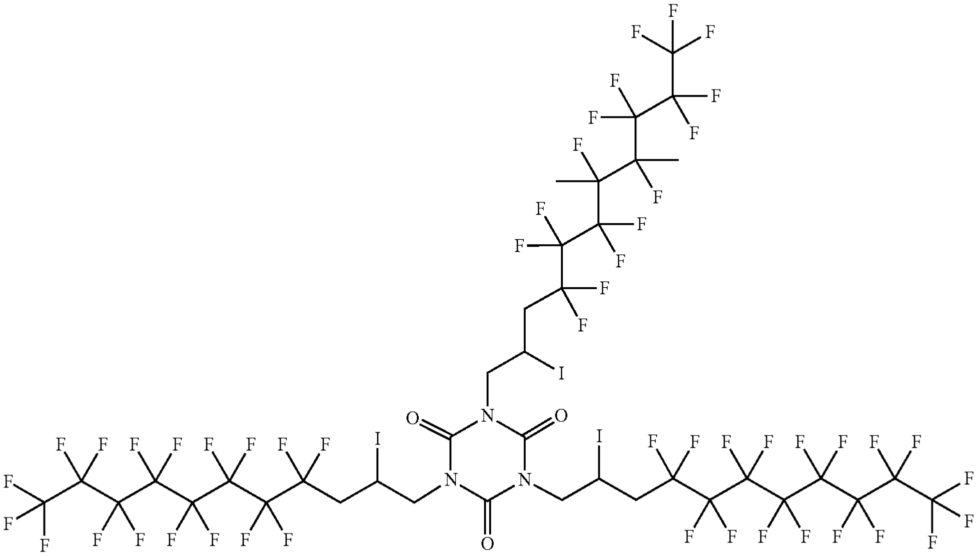
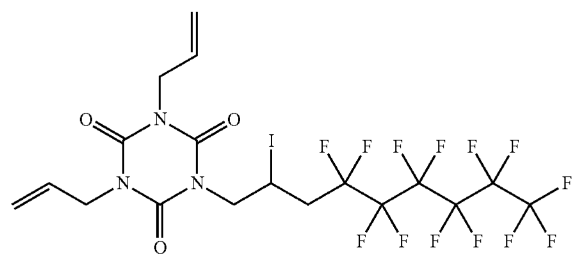
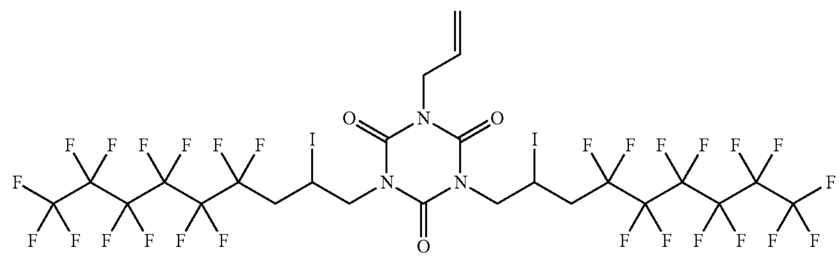
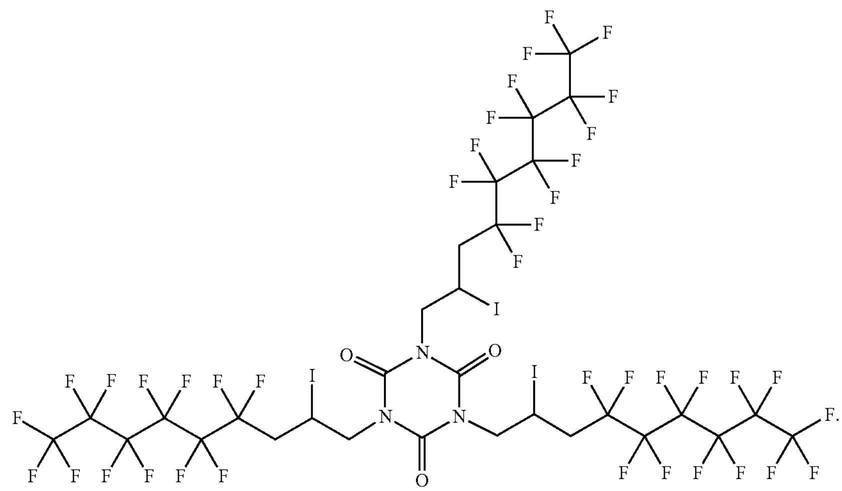

An exemplary embodiment of the present specification provides a method for preparing a compound of the following Chemical Formula 1, the method including: (s1) introducing triallyl isocyanurate, $C_nF_{2n+1}X4$, a base and a solvent and stirring the resulting mixture under nitrogen gas; and (s2) adding a radical initiator thereto and stirring the resulting mixture.

[Chemical Formula 1]

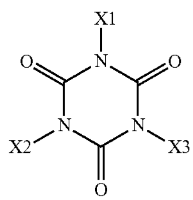

In Step (s1) and Chemical Formula 1,
at least one of X1 to X3 is

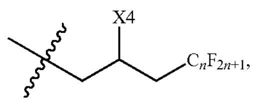

and the others are an allyl group,
n is an integer from 1 to 20,

is a moiety bonded to Chemical Formula 1, and
X4 is a halogen group.

According to an exemplary embodiment of the present specification, the reaction temperature in Step (s1) is 0° C. to room temperature. When the above reaction is performed within the above reaction temperature range, the reaction conditions are not tricky but mild, and side reactions that appear as the temperature rises are suppressed, so that the yield of the compound of Chemical Formula 1, which is a final target, is increased. In addition, various temperature ranges may be set according to the range of n and the molecular weight of the compound of Chemical Formula 1 in Step (s1).

In the present specification, room temperature means 20±5° C. under atmospheric pressure.

The base according to an exemplary embodiment of the present specification may be potassium carbonate ($K_2CO_3$), sodium hydrogen carbonate ($NaHCO_3$), potassium hydrogen carbonate ($KHCO_3$) or any mixture thereof, but is not limited thereto, and a salt used in the related art may be used.

According to an exemplary embodiment of the present specification, the solvent is an organic solvent.

According to an exemplary embodiment of the present specification, the solvent is selected from among hexane, heptane, toluene, benzene, acetonitrile, dichloromethane, dichloroethane, trichloroethane, chloroform, dichloroform, nitromethane, dibromomethane, cyclopentanone, cyclohexanone, fluorobenzene, bromobenzene, chlorobenzene, xylene, mesitylene, ethylacetate or any mixture thereof, but is not limited thereto, and an organic solvent used in the related art may be used.

According to an exemplary embodiment of the present specification, the radical initiator is a water-soluble initiator.

According to an exemplary embodiment of the present specification, the radical initiator is any one of potassium persulfate (KPS), ammonium persulfate (APS), potassium hydrosulfite, sodium hydrosulfite, sodium persulfate, or hydrogen peroxide.

According to an exemplary embodiment of the present specification, the reaction temperature in Step (s2) is 0° C. When Step (s2) is performed at the above reaction temperature, side reactions are suppressed, so that the yield of Chemical Formula 1, which is a final target, is increased.

The mechanism of the preparation method according to an exemplary embodiment of the present specification is described in the following FIG. 1. (1) The radical initiator is dissociated under basic conditions, (2) radicals are generated, and (3) the atom transfer reaction occurs. The hydrogen of the initiator is dissociated in (3) and bonded to a halogen group (an iodine group) bonded to perfluoroalkyl, and the perfluoroalkyl becomes a radical. Thereafter, by the radical chain reaction of (4) and (5), (4) the radicalized perfluoroalkyl group and the allyl group of the triallyl isocyanurate are bonded to form a radical, and (5) the halogen group (the iodine group) bonded to the perfluoroalkyl is bonded to the radical to produce the compound of Chemical Formula 1.

In FIG. 1, $K_a$ is the addition rate constant of a radical to substrate ($R_f$).

According to an exemplary embodiment of the present specification, a step of obtaining the compound of Chemical Formula 1 is further included after Step (s2).

The obtaining of the compound of Chemical Formula 1a according to an exemplary embodiment of the present specification includes:

(s31) a quench and layer separation step;
(s32) a drying step;
(s33) a filtration step;
(s34) a concentration step; and
(s35) an obtaining step.

According to an exemplary embodiment of the present specification, Step (s31) (quench and layer separation step) is a step of terminating the reaction by adding a reaction termination material, and separating the layers.

According to an exemplary embodiment of the present specification, as the reaction termination material of Step (s31), distilled water, an aqueous ammonium chloride solution, an aqueous sodium hydrogen carbonate solution, an aqueous KF (saturated) solution, an aqueous HCl solution, an aqueous NaCl (saturated) solution, chloroform, dichloromethane, ethyl acetate, and the like may be used, but the reaction termination material is not limited thereto. Preferably, as the reaction termination material, an aqueous ammonium chloride solution, an aqueous sodium hydrogen carbonate solution, an aqueous NaCl solution, and ethyl acetate are used.

In Step (s31), the order in which the reaction termination and layer separation are performed is not limited to a specific order. As an exemplary embodiment, reaction termination and layer separation may be simultaneously performed, and as another exemplary embodiment, the reaction is terminated by adding a reaction termination material, and then layers may be separated. However, the progression order is not limited to the above-described example.

Since the radical initiator remaining after the reaction is water-soluble, the radical initiator may be dissolved in water and removed in Step (s31).

According to an exemplary embodiment of the present specification, Step (s32) (drying step) is performed by adding a desiccant to any one layer of the material layer-separated in Step (s31). For example, when chloroform exemplified above is used as the reaction termination material, Step (s32) is performed by adding a desiccant to a chloroform layer which is a lower layer, that is, an organic layer.

Examples of the desiccant include magnesium sulfate, sodium sulfate, and the like, but are not limited thereto. According to a preferred exemplary embodiment, the desiccant is magnesium sulfate.

In the present specification, the desiccant is added in a sufficient amount required for typical drying in the art.

According to an exemplary embodiment of the present specification, Step (s33)(filtration step) may be performed by a method known in the art. As a representative example, it is possible to use a method of inhaling air using an inhaler and filtering impurities including a desiccant, and the like, which are separated from a target product with a filter, or a method of removing other impurities using a solvent that does not dissolve a target product, but dissolves other impurities by utilizing the difference in solubility in a specific solvent.

According to an exemplary embodiment of the present specification, Step (s34)(concentration step) may be performed by a method known in the art. The step may be performed by evaporating the solvent using a vacuum rotary evaporator as a representative example, but the representative example is not limited thereto.

According to an exemplary embodiment of the present specification, additional filtration and drying steps may be added after Step (s34).

It is possible to include a drying step before the obtaining step (s35), and the drying step is a step of drying the compound of Chemical Formula 1. The drying step is different from Step (s32) and may be performed by a method known in the art, representative examples thereof include vacuum oven drying, spray drying, flash drying, and the like, and preferably, the compound of Chemical Formula 1 may be dried by vacuum oven drying.

According to an exemplary embodiment of the present specification, Step (s35) (obtaining step) is a step of obtaining the compound of Chemical Formula 1 which is concentrated (dried) in Step (s34).

According to an exemplary embodiment of the present specification, in the obtaining step, Steps (s32) to (s33) may be performed three or more times, if necessary.

According to an exemplary embodiment of the present specification, provided is a mixture including two or more of the compounds.

According to another exemplary embodiment of the present specification, two or more compounds included in the mixture are the same as or different from each other. That is, it means that the two or more compounds are the same as or different from each other while having the structure of Chemical Formula 1.

According to still another exemplary embodiment of the present specification, the mixture may further include a compound different from the compound of Chemical Formula 1.

According to an exemplary embodiment of the present specification, provided is a single molecule derived from the compound.

In the present specification, for example, the aforementioned "single molecule derived from the compound of Chemical Formula 1" may mean a single molecule in which the allyl group of the compound of Chemical Formula 1 forms a radical and an additional substituent is introduced, a single molecule in which an additional substituent is introduced using the halogen group of Chemical Formula 1 as an electron donor, or the compound of Chemical Formula 1 itself.

According to an exemplary embodiment of the present specification, provided is an oligomer including a monomer derived from the compound.

Those skilled in the art may understand the term "monomer" described in the present specification as a state in which a compound is polymerized to be linked to the main chain of the oligomer.

In the present specification, for example, the "monomer derived from the compound of Chemical Formula 1" is a repeating unit that constitutes the main chain in the polymer, and means that an allyl group of the compound of Chemical Formula 1 may form a radical to become a monomer, and a halogen group may be used as an electron donor to introduce a monomer or end group which makes up the main chain of other oligomers.

Furthermore, radicals generated by the release of the halogen group in the structure may also react with other allyl group-containing oligomers or the above monomers.

According to an exemplary embodiment of the present specification, the oligomers may have the following structures, but is not limited thereto. Although only the case where n in Chemical Formula 1 is 4, 6, or 8 is illustrated for the following structure, oligomers with various structures may be shown depending on the range of n in Chemical Formula 1, that is, n from 1 to 20.

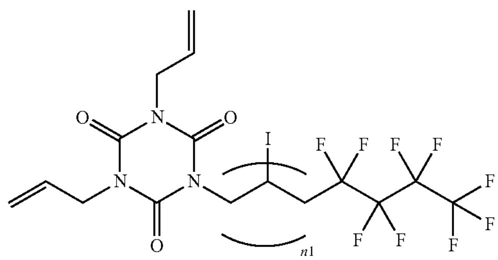

-continued
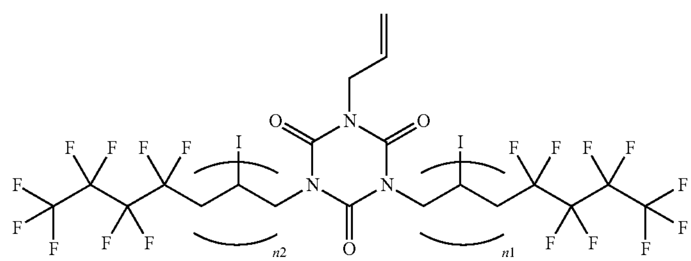
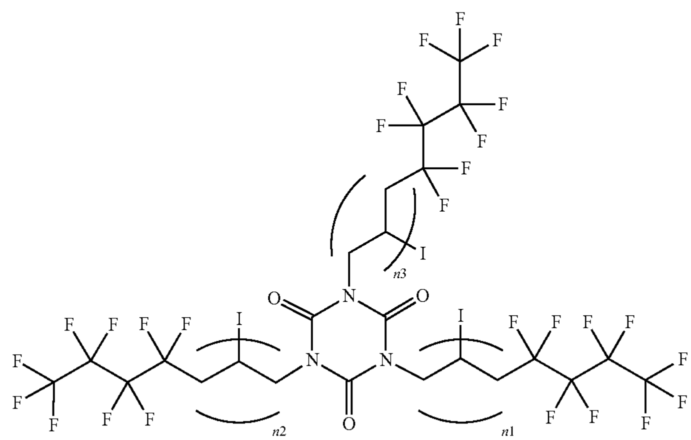
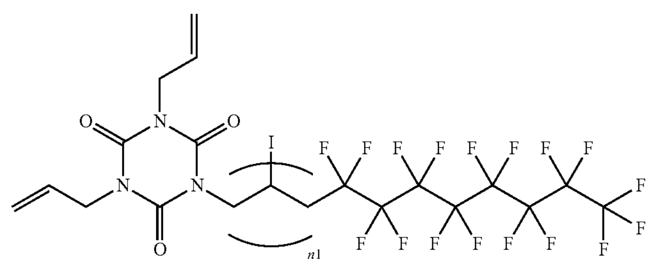
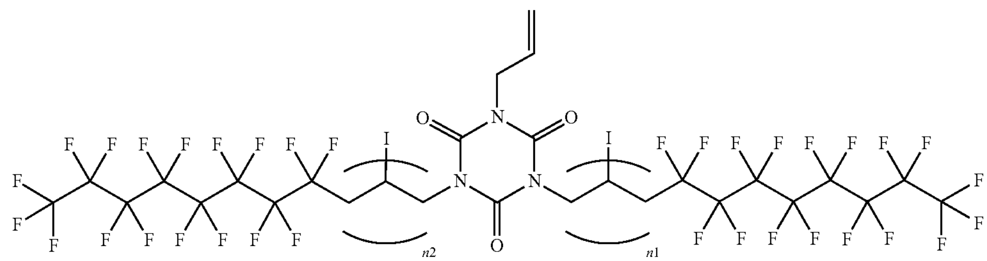

-continued
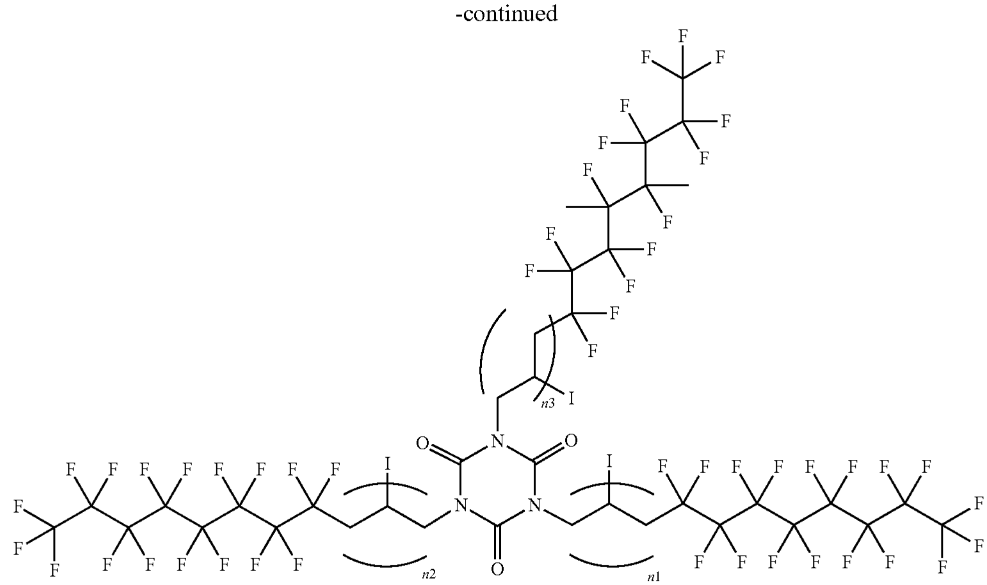
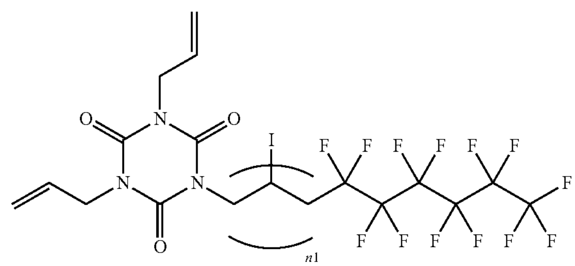
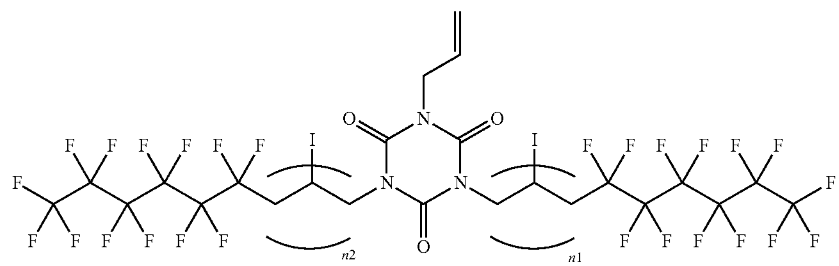
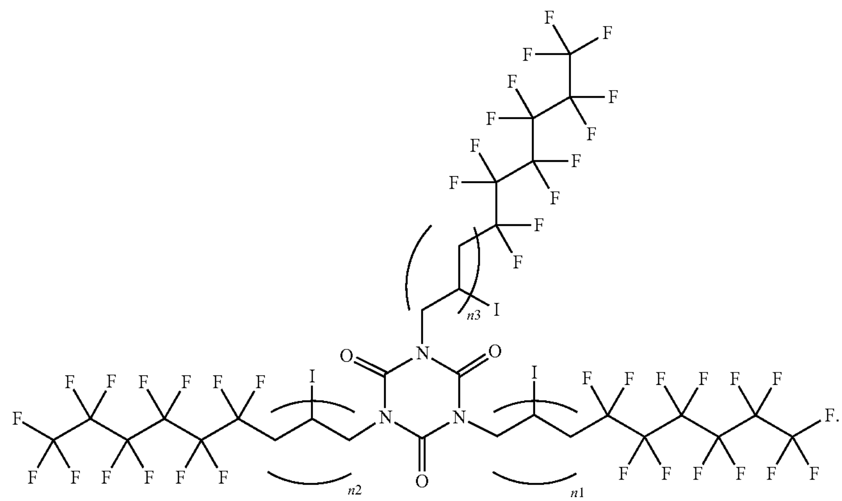

In the structures, n1 to n3 are each an integer of 2 or higher.

According to an exemplary embodiment of the present specification, n1 to n3 are each an integer from 2 to 10,000, preferably an integer from 2 to 5,000, more preferably an integer from 2 to 1000, and even more preferably an integer from 2 to 100.

The compound according to an exemplary embodiment of the present specification, and a single molecule and an oligomer derived therefrom include a good release group and a structure capable of being cross-linked, so that various derivatives can be prepared.

MODE FOR INVENTION

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to explain the present specification more completely to a person with ordinary skill in the art.

Example 1

After 9.9 g of triallyl isocyanurate, 0.101 g of $NaHCO_3$ and 20.7 mL of nonafluoro-1-iodobutane were dissolved in 100 mL of water and 50 mL of acetonitrile in a 250 mL two-neck round-bottom flask and $N_2$ bubbling was performed at room temperature for 30 minutes, $Na_2S_2O_4$ was added thereto in a powder state, and then the resulting mixture was stirred at 0° C. for 17 hours. Thereafter, after the aqueous layer was extracted three times with 200 mL of chloroform, the organic layer was washed with water, and the washed organic layer was dried over 10 g of $MgSO_4$. Thereafter, filtration was performed and the solvent was evaporated to obtain 44 g of a product from which perfluorobutyl iodide was derived, and the weight ratios of Compound 1-2, Compound 1-3 and Oligomer 1 are shown in the following Table 1 by determining the detailed composition of the product by $^1H$-NMR.

[Compound 1-1]

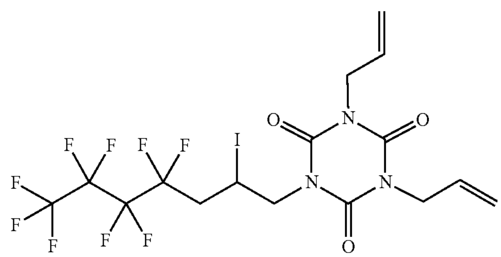

Molecular Weight: 595.20

[Compound 1-2]

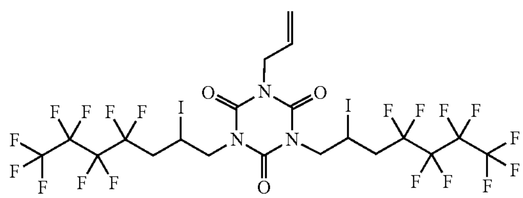

Molecular Weight: 941.14

-continued

[Compound 1-3]

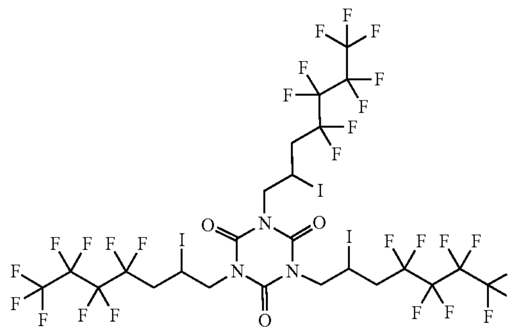

Molecular Weight: 1287.07

TABLE 1

| Structure | Compound 1-2 | Compound 1-3 | Oligomer 1 |
|---|---|---|---|
| Weight ratio | 80 to 90 | 1 to 10 | 1 to 10 |

Example 2

After 9.9 g of triallyl isocyanurate, 0.101 g of $NaHCO_3$ and 10.3 mL of nonafluoro-1-iodobutane were dissolved in 100 mL of water and 50 mL of acetonitrile in a 250 mL two-neck round-bottom flask and $N_2$ bubbling was performed at room temperature for 30 minutes, $Na_2S_2O_4$ was added thereto in a powder state, and then the resulting mixture was stirred at 0° C. for 17 hours. Thereafter, after the aqueous layer was extracted three times with 200 mL of chloroform, the organic layer was washed with water, and the washed organic layer was dried over 10 g of $MgSO_4$. Thereafter, filtration was performed and the solvent was evaporated to obtain 22 g of a product from which perfluorobutyl iodide was derived, and the weight ratios of Compound 1-1, Compound 1-2 and Oligomer 1 are shown in the following Table 2 by determining the detailed composition of the product by $^1H$-NMR.

TABLE 2

| Structure | Compound 1-1 | Compound 1-2 | Oligomer 1 |
|---|---|---|---|
| Weight ratio | 70 to 80 | 10 to 20 | 1 to 10 |

Oligomer 1 of Examples 1 and 2 is derived from any one or more of Compounds 1-1 to 1-3, and has a molecular weight that exceeds a molecular weight of Compound 1-3 that is the maximum unit as a single molecule.

Example 3

After 9.97 g of triallyl isocyanurate, 0.101 g of $NaHCO_3$ and 31.7 mL of heptadecafluoro-n-octyl iodide were dissolved in 100 mL of water and 40 mL of acetonitrile in a 250 mL two-neck round-bottom flask and $N_2$ bubbling was performed at 0° C. for 30 minutes, $Na_2S_2O_4$ was added thereto in a powder state, and then the resulting mixture was stirred at 0° C. for 17 hours. Thereafter, after the aqueous layer was extracted three times with 200 mL of chloroform, the organic layer was washed with water, and the washed organic layer was dried over 10 g of $MgSO_4$. Thereafter, filtration was performed and the solvent was evaporated to obtain 53 g of a product from which perfluorooctyl iodide was derived, and the weight ratios of Compound 2-2, Compound 2-3 and Oligomer 2 are shown in the following Table 3 by determining the detailed composition of the product by $^1$H-NMR.

Example 4

After 9.97 g of triallyl isocyanurate, 0.101 g of $NaHCO_3$ and 15.8 mL of heptadecafluoro-n-octyl iodide were dissolved in 100 mL of water and 40 mL of acetonitrile in a 250 mL two-neck round-bottom flask and $N_2$ bubbling was

[Compound 2-1]

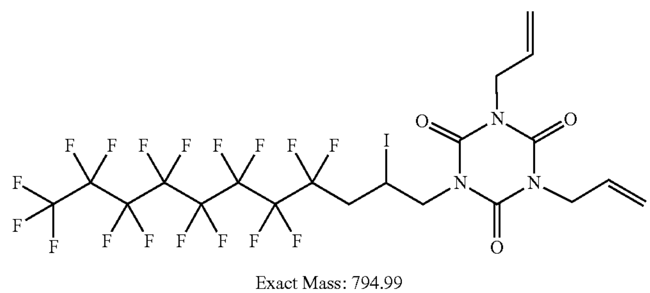

Exact Mass: 794.99

[Compound 2-2]

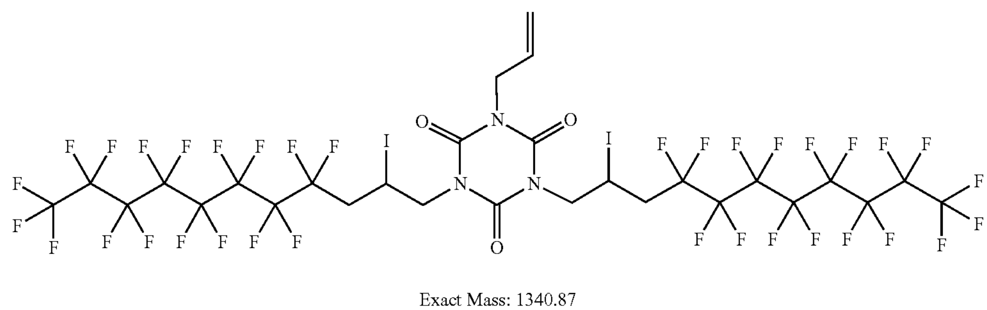

Exact Mass: 1340.87

[Compound 2-3]

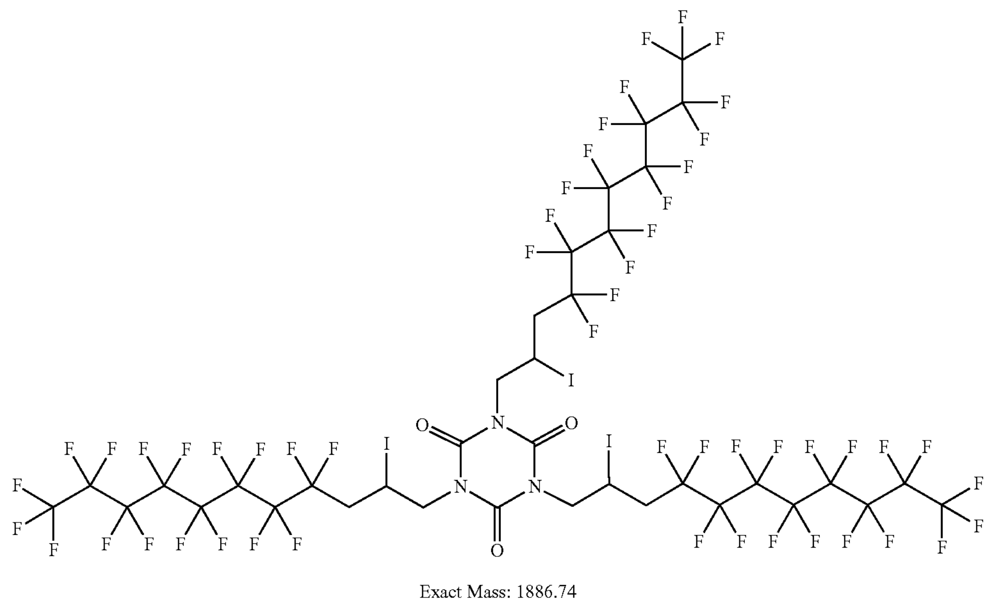

Exact Mass: 1886.74

TABLE 3

| Structure | Compound 2-2 | Compound 2-3 | Oligomer 2 |
|---|---|---|---|
| Weight ratio | 10 to 20 | 80 to 90 | 1 to 10 |

performed at 0° C. for 30 minutes, $Na_2S_2O_4$ was added thereto in a powder state, and then the resulting mixture was stirred at 0° C. for 17 hours. Thereafter, after the aqueous layer was extracted three times with 200 mL of chloroform, the organic layer was washed with water, and the washed organic layer was dried over 10 g of $MgSO_4$. Thereafter, filtration was performed and the solvent was evaporated to obtain 36 g of a product from which perfluorooctyl iodide was derived, and the weight ratios of Compound 2-1, Compound 2-2 and Oligomer 2 are shown in the following Table 4 by determining the detailed composition of the product by $^1$H-NMR.

TABLE 4

| Structure | Compound 2-1 | Compound 2-2 | Oligomer 2 |
|---|---|---|---|
| Weight ratio | 40 to 50 | 40 to 50 | 1 to 10 |

Oligomer 2 of Examples 3 and 4 is derived from any one or more of Compounds 2-1 to 2-3, and has a molecular weight that exceeds a molecular weight of Compound 2-3 that is the maximum unit as a single molecule.

The compound of Chemical Formula 1 prepared in Tables 1 to 4 includes a perfluoroalkyl group including fluorine having the effects of achieving low relative permittivity and low dissipation factor, and is used as a polyfunctional monomer as a triallyl isocyanurate derivative that serves as a cross-linking agent, so that it is possible to exhibit the effects of achieving low refractive index, low relative permittivity, low surface energy and low dissipation factor. The compound of Chemical Formula 1 may be used for various uses.

The compound of Chemical Formula 1 may be used as a material for circuit boards, the relative permittivity is predicted to be about Dk=2.5 (Reference=2.6 or higher) in a specific composition, and through the aforementioned result, it can be predicted that there is an effect of lowering the relative permittivity.

Reference: Triallyl isocyanurate

The invention claimed is:

1. A compound of Chemical Formula 1:

[Chemical Formula 1]

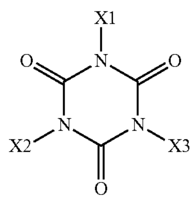

wherein, at least one of X1 to X3 is

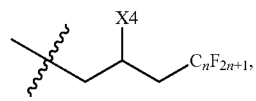

and the others are an allyl group, n is an integer from 1 to 20, is a moiety bonded to Chemical Formula 1, and X4 is a halogen group.

2. The compound of claim 1, wherein X4 is an iodine group (—I).

3. The compound of claim 1, wherein the

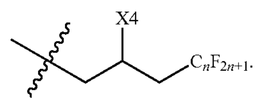

is any one of the following structures:

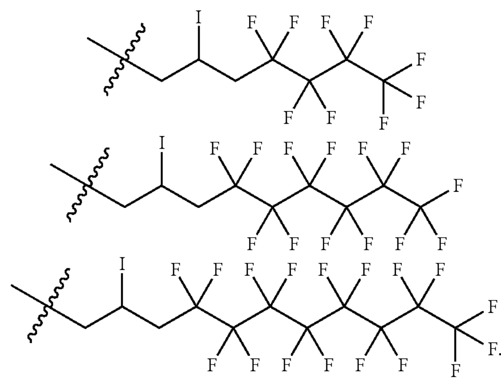

4. The compound of claim 1, wherein the Chemical Formula 1 is any one selected from the following compounds:

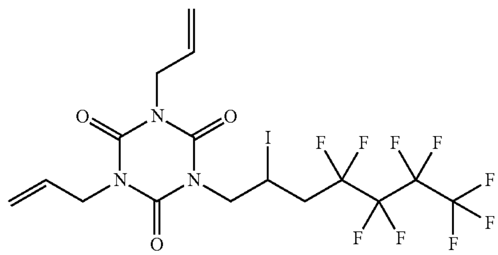

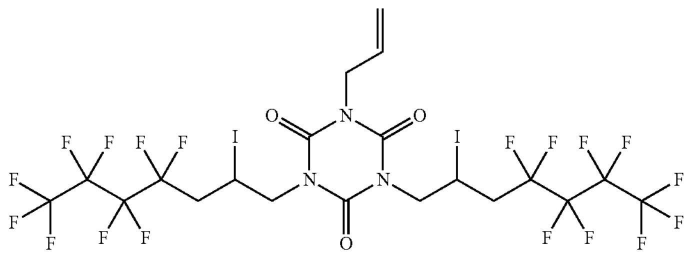

-continued
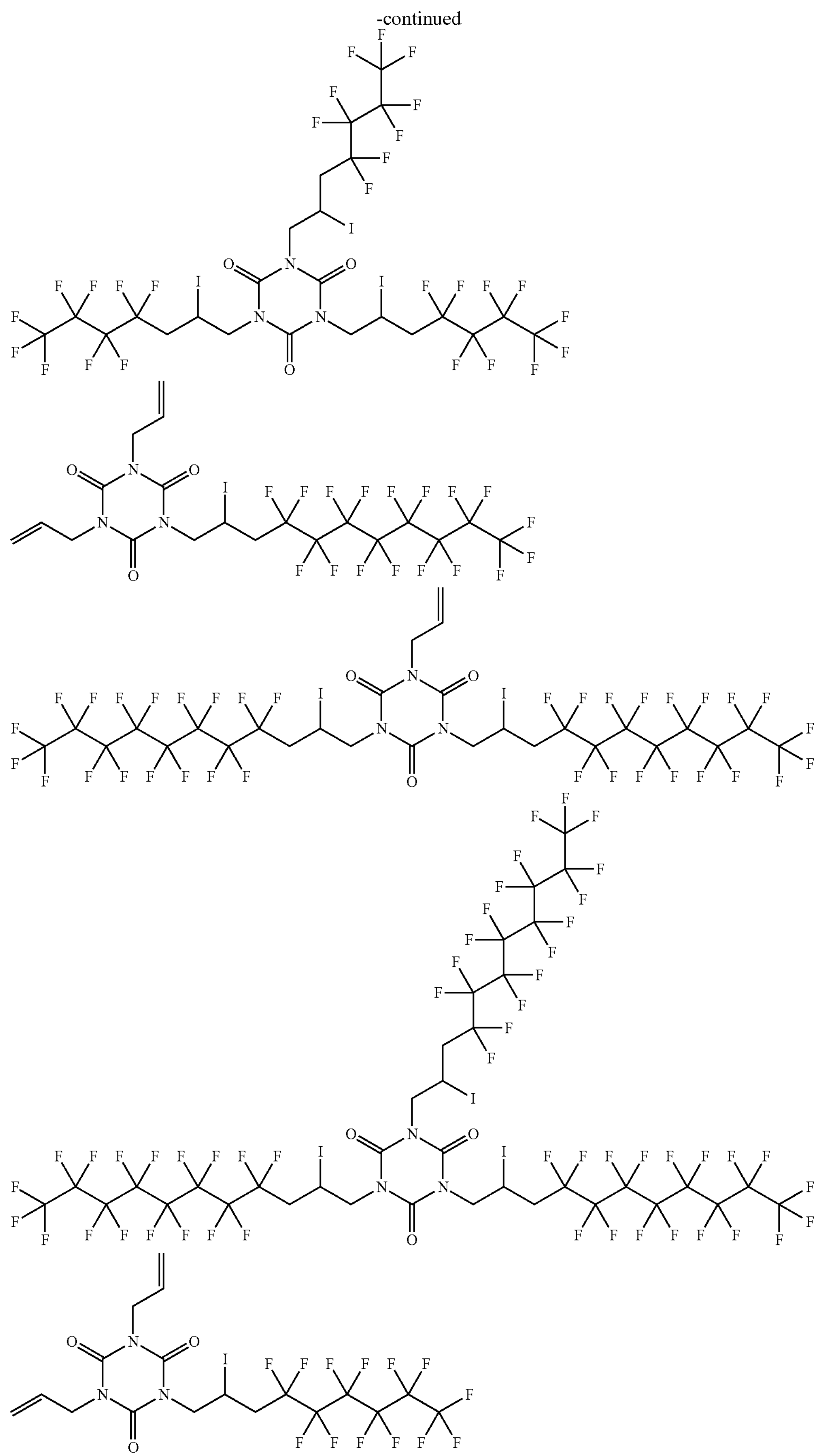

-continued

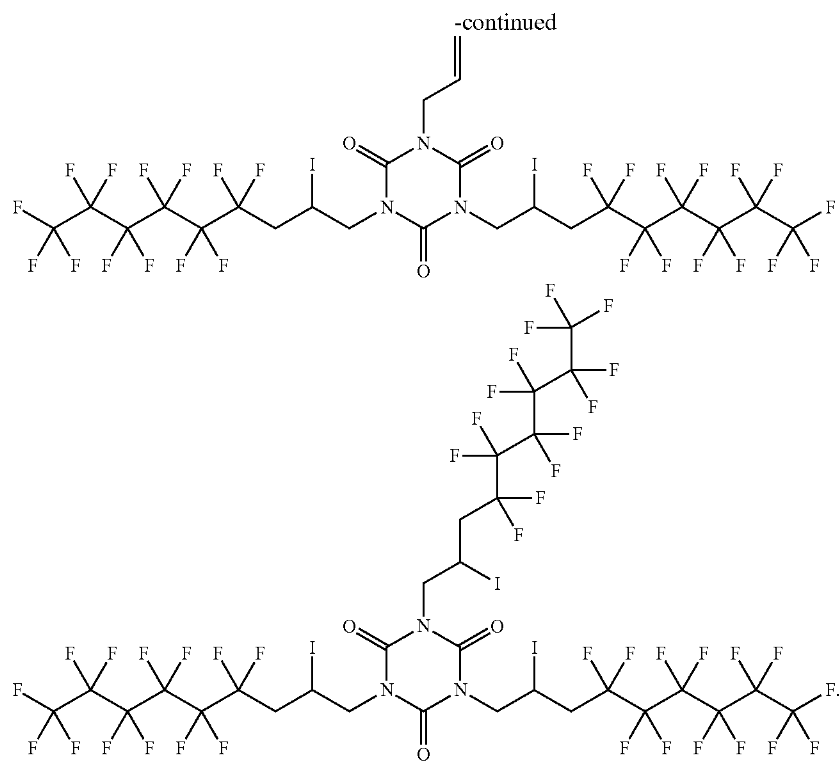

5. A method for preparing a compound of Chemical Formula 1, the method comprising: (s1) putting triallyl isocyanurate, $C_nF_{2n+1}X4$, a base, and a solvent into a container to prepare a mixture and stirring the resulting mixture under nitrogen gas; and (s2) adding a radical initiator thereto and stirring thereof to prepare the compound:

[Chemical Formula 1]

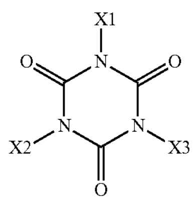

wherein, in the Step (s1), at least one of X1 to X3 is

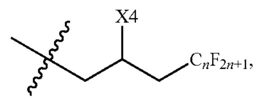

and the others are an allyl group, n is an integer from 1 to 20, and

X4 is a halogen group.

* * * * *